United States Patent [19]

Jackson

[11] 4,031,227

[45] June 21, 1977

[54] SUBSTITUTED 2H,3H-2,1-BENZISOTHIAZOLE-S-OXIDES, METHOD OF USE AND PHARMACEUTICAL COMPOSITIONS THEREOF

[75] Inventor: Thomas E. Jackson, Madison, N.J.

[73] Assignee: Sandoz, Inc., E. Hanover, N.J.

[22] Filed: Sept. 18, 1975

[21] Appl. No.: 614,380

[52] U.S. Cl. .............................. 424/270; 260/304 A
[51] Int. Cl.² .......................................... C07D 275/06
[58] Field of Search ................ 260/304 A; 424/270

[56] References Cited
OTHER PUBLICATIONS

Williams et al., J. Am. Chem. Soc., 93 (26), 12–1971.

Primary Examiner—R. J. Gallagher
Attorney, Agent, or Firm—Gerald D. Sharkin; Richard E. Vila; Joseph J. Borovian

[57] ABSTRACT

The invention discloses substituted 2H,3H-2,1-benzisothiazole-S-oxides having pharmacological activity in animals and useful as CNS depressant agents. The compounds may be prepared by reacting a substituted 2H,3H-2,1-benzisothiazole with an oxidizing agent. The substituted 2H,3H-2,1-benzisothiazole may be prepared by reacting a substituted α-methylthio-o-toluidine with one equivalent of an oxidizing agent, followed by treatment with base.

19 Claims, No Drawings

SUBSTITUTED 2H,3H-2,1-BENZISOTHIAZOLE-S-OXIDES, METHOD OF USE AND PHARMACEUTICAL COMPOSITIONS THEREOF

The compounds 2-methyl-5-chloro-2H,3H-2,1-benzisothiazole-S-oxide and 2-methyl-5-cyano-2H,3H-2,1-benzisothiazole-S-oxide have been previously disclosed in the literature by P. Claus et al, Tet. Letters, 37, 3319–3322 (1974). To my knowledge, no pharmacological activity has been heretofore associated with any of these compounds.

The present invention relates to substituted 2H,3H-2,1-benzisothiazole-S-oxides and to their use as CNS depressant agents. The invention also relates to pharmaceutical compositions containing the above compounds as an active ingredient thereof and to the method of using such compositions as CNS depressants, particularly for inducing sleep and as tranquilizers.

The compounds of this invention may be represented by the following structural formula I:

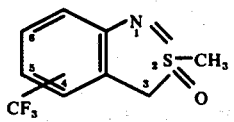

wherein the $CF_3$ group is in the 4-, 5- or 6-position.

The compounds of formula I may be prepared by the following reaction scheme:

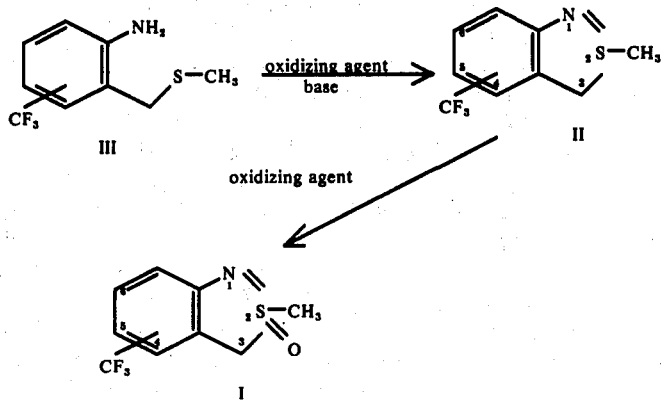

wherein the position of the $CF_3$ group with respect to structures I and II is as defined above and the $CF_3$ group with respect to structure III is meta- or para- to the amino group.

The preparation of compounds of formula I involves the reaction of a substituted 2H,3H-2,1-benzisothiazole of formula II above with not more than an equimolar amount of an oxidizing agent in the presence of an inert, organic solvent which is adapted to dissolving the reactants and product compounds of formula I. Suitable solvents are known and available and include, by way of illustration, the chlorinated hydrocarbons, lower alkanols, e.g., ethanol, and esters, e.g., dioxane, tetrahydrofuran, etc. Aqueous solvent mixtures may also be employed to dissolve the reactants and product compounds of formula I. The reaction is preferably effected employing a peracid, e.g., m-chloro-peroxybenzoic acid, in the presence of a chlorinated hydrocarbon, e.g., methylene chloride. The temperature of the reaction is not critical, but it is preferred that the reaction be carried out at temperatures in the range of from about −35° to 70° C. and, most preferably, from about −20° to 10° C. The reaction product of formula I may be isolated from the reaction mixture employing conventional techniques.

The preparation of compounds of formula II involves reacting a substituted α-methylthio-o-toluidine of formula III above with not more than one equivalent of an oxidizing agent in the presence of an inert, organic solvent, followed by treatment with an inorganic base. Suitable solvents are as described above with respect to the preparation of compounds of formula I. Suitable inorganic bases include alkali metal hydroxides, e.g., sodium hydroxide, potassium hydroxide and the like, or sodium hydride, the first-named being especially preferred. The reaction is preferably effected employing N-chlorosuccinimide as an oxidizing agent in the presence of a chlorinated hydrocarbon, e.g., methylene chloride. The temperature of the reaction is not critical, but it is preferred that the reaction be carried out at temperatures in the range of from about −50° to 70° C. and, most preferably, from about −40° to 20° C. The reaction product of formula II may be isolated from the reaction mixture by working up by conventional techniques; however, due to its relatively poor stability, it is preferred that the reaction continue to the preparation of compounds of formula I.

The compounds of formula III are either known or can be prepared in conventional manner from available materials, e.g., by the procedures of Gassman and Greutzmacher, J. Amer. Chem. Soc. 96 (17), 5487–5495 (1974) or by the procedures of Claus, Vycudilik and Rieder, Monatsh. Chem. 102, 1571–1582 (1971).

The compounds of formula I are useful because they possess pharmocological activity in animals. In particular, the compounds effect a depression of the central nervous system and are useful as sleep inducers and minor tranquilizers as indicated: (1) by a reinduction of hexobarbital anesthesia in mice (10–200 mg/kg i.p.) according to the method of Winter, J. Pharmacol. and Exp. Therap., 94, 7–11, 1948; (2) by their ability to produce docility and muscle relaxation in behavior tests in mice given 10 to 200 mg/kg i.p. of test compound according to the 30-word adjective check sheet system, basically described by S. Irwin, Gordon Research Conference, Medicinal Chemistry, 1949 and Chem. Symposium on Sedative and Hypnotic Drugs, Williams and Wilkins, 1954; and (3) by scoring for loss of righting reflex according to the method of Reed-Muench (American Journal of Hygiene, 27: 493:497, 1938), in which mice are administered 12.5 mg./kg. i.p. Thioridazine, immediately after which the test compound is administered at dosages of 5 to 200 mg/kg i.p. in a volume of 0.1 ml./10 g. body weight. Sixty minutes after dosing, the mice are scored for loss of righting reflex.

For such uses, the compounds may be combined with one or more pharmaceutically acceptable carriers or adjuvants, and may be administered orally in such forms as tablets, capsules, dispersible powders, granules, syrups, elixirs, suspensions, and the like, or parenterally in the forms of sterile injectable solutions or suspensions. These pharmaceutical preparations may contain up to about 90% active ingredient in combination with the carrier or adjuvant. The preferred pharmaceutical compositions from the standpoint of preparation and ease of administration are solid compositions, particularly hard-filled capsules and tablets.

The dosage administered will vary depending upon known variables such as the particular compound, the mode of administration and the severity of the condition being treated. As sleep inducers, in general, satisfactory results are obtained when the compounds are administered at a daily dosage of from about 2 milligrams to about 100 milligrams per kilogram of animal body weight, typically given orally and in a single dose at bedtime. For most large mammals, the administration of from about 150 milligrams to about 1000 milligrams of the compound per day provides satisfactory results with a single dose of from 150 to 1000 milligrams, preferably 150 to 500 milligrams, being given at bedtime. For use as tranquilizers, in general, satisfactory results are obtained when the compounds are administered at a daily dosage of from about 4 milligrams to about 200 milligrams per kilogram of animal body weight, typically given orally and in divided doses, three or four times per day. For most large mammals, the total daily dosage is from about 300 to about 2000 milligrams, and dosage forms suitable for internal administration comprise from about 75 to about 1000 milligrams, preferably 75 to 500 milligrams, of the compound.

Tablets and capsules containing the ingredients below may be prepared by conventional techniques and are useful for inducing sleep at a dose of one tablet or capsule at bedtime.

| Ingredients | Weight (mg.) Tablet | Capsule |
| --- | --- | --- |
| 2-methyl-5-trifluoromethyl-2H,3H-2,1-benzisothiazole-S-oxide | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

Representative formulations of a tablet and a capsule prepared by conventional techniques and useful as minor tranquilizers at a dose of one tablet or capsule 4 times a day are as follows:

| Ingredients | Weight (mg.) Tablet | Capsule |
| --- | --- | --- |
| 2-methyl-5-trifluoromethyl-2H,3H-2,1-benzisothiazole-S-oxide | 100 | 100 |
| tragacanth | 10 | — |
| lactose | 197.5 | 250 |
| corn starch | 25 | — |
| talcum | 15 | — |
| magnesium stearate | 2.5 | — |
| Total | 350 mg. | 350 mg. |

The following examples are merely illustrative of specific compounds of the invention and the manner in which they may be prepared.

EXAMPLE 1

2-Methyl-5-trifluoromethyl-2H,3H-2,1-benzisothiazole-S-oxide

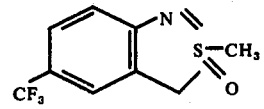

To 10.2 g. of α-methylthio-4-trifluoromethyl-o-toluidine predissolved in 50 ml. of methylene chloride and cooled to −38° C. is added dropwise, over 40 minutes, a solution of 6.2 g. of N-chlorosuccinimide predissolved in 250 ml. of methylene chloride, while the temperature is maintained between −28° and −38° C. After an additional 8 minutes, 13.3 ml. of a 15% aqueous sodium hydroxide solution is added, the cold bath is removed and the reaction mixture allowed to warm to 5° C. To the reaction mixture is added 100 ml. of water, the mixture is shaken, and the phases are separated. The methylene chloride layer is cooled to −20° C. and treated with a solution of 9.7 g. of m-chloroperoxybenzoic acid predissolved in 150 ml. of methylene chloride, added dropwise over 10 minutes. The cold bath is removed and the reaction mixture stirred for 20 minutes, after which time, it is washed successively with an aqueous solution of sodium sulfite and sodium bicarbonate and a saturated aqueous solution of sodium bicarbonate. The phases are separated and the methylene chloride layer is dried, evaporated in vacuo to dryness, and the residue recrystallized from chloroform/petroleum ether to yield 2-methyl-5-trifluoromethyl-2H,3H-2,1-benzisothiazole-S-oxide, m.p. 151°–154° C.

EXAMPLE 2

Following the procedure of Example 1, but employing appropriate starting materials in approximately equivalent amounts, the following additional compounds are prepared:
A. 2-methyl-4-trifluoromethyl-2H,3H-2,1-benzisothiazole-S-oxide, m.p. 120°–124° C., and
B. 2-methyl-6-trifluoromethyl-2H,3H-2,1-benzisothiazole-S-oxide, m.p. 106°–110° C.

What is claimed is:
1. A compound of the formula:

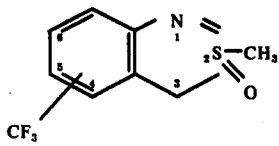

wherein the CF₃ group is in the 4-, 5- or 6-position.

2. The compound of claim 1 which is 2-methyl-5-trifluoromethyl-2H,3H-2,1-benzisothiazole-S-oxide.

3. The compound of claim 1 which is 2-methyl-6-trifluoromethyl-2H,3H-1,2-benzisothiazole-S-oxide.

4. A pharmaceutical composition for inducing sleep in mammals comprising an inert pharmaceutically acceptable carrier and a sleep-inducing effective amount of a compound of claim 1.

5. The pharmaceutical composition of claim 4 wherein the compound is 2-methyl-5-trifluoromethyl-2H,3H-b 2,1-benzisothiazole-S-oxide.

6. The pharmaceutical composition of claim 4 wherein the compound is 2-methyl-6-trifluoromethyl-2H,3H-2,1-benzisothiazole-S-oxide.

7. A pharmaceutical composition of claim 4 in unit dosage form and comprising from 150 to 1000 milligrams of the compound.

8. A pharmaceutical composition for effecting tranquilization in mammals comprising an inert pharmaceutically acceptable carrier and a tranquilizing effective amount of a compound of claim 1.

9. The pharmaceutical composition of claim 8 wherein the compound is 2-methyl-5-trifluoromethyl-2H,3H-2,1-benzisothiazole-S-oxide.

10. The pharmaceutical composition of claim 8 wherein the compound is 2-methyl-6-trifluoromethyl-2H,3H-2,1-benzisothiazole-S-oxide.

11. A pharmaceutical composition of claim 8 in unit dosage form and comprising from 75 to 1000 milligrams of the compound.

12. A method of inducing sleep in mammals comprising orally or parenterally administering to a mammal prior to sleep a sleep-inducing effective amount of a compound of claim 1.

13. The method of claim 12 wherein the compound administered is 2-methyl-5-trifluoromethyl-2H,3H-2,1-benzisothiazole-S-oxide.

14. The method of claim 12 wherein the compound administered is 2-methyl-6-trifluoromethyl-2H,3H-2,1-benzisothiazole-S-oxide.

15. A method of claim 12 wherein the compound is administered in a daily amount of from 150 to 1000 milligrams.

16. A method of effecting tranquilization in mammals comprising orally or parenterally administering to a mammal in need of such treatment a tranquilizing-effective amount of a compound of claim 1.

17. The method of claim 16 wherein the compound administered is 2-methyl-5-trifluoromethyl-2H,3H-2,1-benzisothiazole-S-oxide.

18. The method of claim 16 wherein the compound administered is 2methyl-6-trifluoromethyl-2H,3H-2,1-benzisothiazole-S-oxide.

19. A method of claim 16 wherein the compound is administered in a daily amount of from 300 to 2000 milligrams.

* * * * *